US010123988B2

(12) United States Patent
Donello et al.

(10) Patent No.: US 10,123,988 B2
(45) Date of Patent: Nov. 13, 2018

(54) COMPOSITIONS INCLUDING ENCAPSULATED ISOTRETINOIN AND METHODS FOR USE THEREOF

(71) Applicant: Allergan, Inc., Irvine, CA (US)

(72) Inventors: John E. Donello, Dana Point, CA (US); Rong Yang, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 78 days.

(21) Appl. No.: 14/208,960

(22) Filed: Mar. 13, 2014

(65) Prior Publication Data

US 2014/0271875 A1 Sep. 18, 2014

Related U.S. Application Data

(60) Provisional application No. 61/789,212, filed on Mar. 15, 2013.

(51) Int. Cl.
*A61K 31/203* (2006.01)
*A61K 9/06* (2006.01)
*A61K 9/00* (2006.01)
*A61K 47/34* (2017.01)
*A61K 9/16* (2006.01)

(52) U.S. Cl.
CPC .......... *A61K 31/203* (2013.01); *A61K 9/0014* (2013.01); *A61K 9/06* (2013.01); *A61K 9/1641* (2013.01); *A61K 47/34* (2013.01)

(58) Field of Classification Search
CPC .. A61K 31/203; A61K 9/0014; A61K 9/1617; A61K 9/1641; A61K 9/1647; A61K 9/1652; A61K 9/1658; A61K 47/30; A61K 47/34; A61K 47/36; A61K 47/38; A61K 47/42

See application file for complete search history.

(56) References Cited

U.S. PATENT DOCUMENTS

| | | | |
|---|---|---|---|
| 5,869,079 A | 2/1999 | Wong et al. | |
| 6,764,698 B1* | 7/2004 | Byun | A61K 9/1647 424/426 |
| 2003/0077297 A1* | 4/2003 | Chen | A61K 9/1617 424/400 |
| 2005/0003007 A1 | 1/2005 | Boix et al. | |

(Continued)

FOREIGN PATENT DOCUMENTS

| | | |
|---|---|---|
| WO | 2012-031205 | 2/2012 |
| WO | 2012-125941 | 9/2012 |

OTHER PUBLICATIONS

Shah et al., "Solid lipid nanoparticles (SLN) of tretinoin: Potential in topical delivery", Int J Pharmaceutics 345: 163-171 (2007).*

(Continued)

*Primary Examiner* — Thor Nielsen
(74) *Attorney, Agent, or Firm* — Laura L. Wine

(57) ABSTRACT

The present invention provides topical dermal compositions including microsphere encapsulated isotretinoin. Pharmaceutically acceptable salts, esters, or amides of isotretinoin are also contemplated for use in the practice of the invention. The compositions of the invention are useful for treating a variety of conditions associated with excess sebum production, such as, for example, acne.

6 Claims, 3 Drawing Sheets

(56) References Cited

U.S. PATENT DOCUMENTS

2006/0222716 A1* 10/2006 Schwarz ............ A61K 9/5123
424/489
2008/0182909 A1 7/2008 Schwendeman
2011/0076318 A1 3/2011 Hughes

OTHER PUBLICATIONS

Cirpanli et al., "Formulation and in-vitro characterization of retinoic acid loaded poly lactic-co-glycolic acid microspheres", J Microencapsul 22: 877-889 (2005).*

Euliss et al., "Imparting size, shape, and composition control of materials for nanomedicine", Chem Soc Rev 35: 1095-1104 (2006).*

Propylene Glycol Monostearate—Chemical Book—technical data sheet.*

Liu et al., "Isotretinoin-loaded solid lipid nanoparticles with skin targeting for topical delivery", Int J Pharmaceutics 328: 191-195 (2007).*

Propylene Glycol Monostearate—Chemical Book.*

Ng et al., "Analysis of nano drug carriers towards optimum release rate", J Med Eng Technol 31: 243-252 (2007).*

Müler et al., "Solid lipid nanoparticles (SLN) and nanostructured lipid carriers (NLC) in cosmetic and dermatological preparations", Adv Drug Delivery Reviews 54 (Suppl 1): S131-S155 (2002).*

Liu et al., "Isotretinoin-loaded solid lipid nanoparticles with skin targeting for topical delivery", Int J Pharmaceutics 328: 191-195 (2007) (Year: 2007).*

Abramovits, William, et al., Sebum, Cosmetics, and Skin Care, Dermatologic Aspects of Cosmetics, Oct. 2000, 617-620, 18(4).

Heller, Jorge, Biodegradable Polymers in Controlled Drug Delivery, Critical Reviews in Therapeutic Drug Carrier Systems, 1987, 39-90, 1 (1).

International Search Report and Written Opinion, PCT/US2014/026420, International Filing Date Mar. 13, 2014, dated Aug. 21, 2014.

Liu, Jie, et al., Isotretinoin-Loaded Solid Lipid Nanoparticles with Skin Targeting for Topical Delivery, International Journal of Pharmaceutics, 2007, 191-195, 328.

Rolland, Alain, et al., Site-Specific Drug Delivery to Pilosebaceous Structures Using Polymeric Microspheres, Pharmaceutical Research, 1993, 1738-1744, 10(12).

United States Pharmacopeia, The National Formulary, USP23, 1995, 1790-1798, 18.

* cited by examiner

COMPOSITIONS INCLUDING ENCAPSULATED ISOTRETINOIN AND METHODS FOR USE THEREOF

CROSS REFERENCE TO RELATED APPLICATIONS

This application claims the benefit of U.S. Provisional Application Ser. No. 61/789,212 filed on Mar. 15, 2013, which is incorporated by reference herein in its entirety.

BACKGROUND OF THE INVENTION

Human skin is composed of three primary layers: the stratum corneum, the epidermis, and the dermis. The outer layer is the stratum corneum. Its primary function is to serve as a barrier to the external environment. Lipids are secreted to the surface of the stratum corneum, where they decrease the stratum corneum's water permeability. Sebum typically constitutes 95% of these lipids. Abramovits et al., *Dermatologic Clinics,* 18:4 (2000). In addition to maintaining the epidermal permeability barrier, sebum transports anti-oxidants to the surface of the skin and protects against microbial colonization.

Sebum is produced in the sebaceous glands. These glands are present over most of the surface of the body. The highest concentration of these glands occurs on the scalp, the forehead, and the face. Despite the important physiological role that sebum plays, many individuals experience excess sebum production, especially in the facial area. An increased rate of sebum excretion is termed seborrhoea.

Seborrhoeic dermatitis is also associated with seborrhea. The condition is characterized by the appearance of red, flaking, greasy areas of skin, most commonly on the scalp, nasolabial folds, ears, eyebrows and chest. In the clinical literature seborrhoeic dermatitis may be also referred to as "sebopsoriasis," "seborrhoeic eczema," "dandruff," and "pityriasis capitis." Yeast infections are a causative factor in seborrhoeic dermatitis. The yeast thrives on sebum and leaves high concentrations of unsaturated fatty acids on the skin, thereby irritating it.

Acne vulgaris is associated with clinical seborrhea and there is a direct relationship between the sebum excretion rate and the severity of acne vulgaris. Although sebum production increases during adolescence (particularly in boys, because of androgen stimulation), increased sebum alone does not cause acne. Bacteria, most importantly *P. acnes,* feed on sebum and as a result are present in increased numbers in persons who have acne. Much of the inflammation associated with acne arises from the action of enzymes produced by the bacteria.

Acne vulgaris is characterized by areas of skin with seborrhea (scaly red skin), comedones (blackheads and whiteheads), papules (pinheads), pustules (pimples), nodules (large papules), and in more severe cases, scarring. It mostly affects skin with the densest population of sebaceous follicles, such as the face, upper chest, and back.

There are four key pathogenic factors of acne:
Follicular hyperkeratinization
*Propionibacterium acnes* (*P. acnes*)
Inflammation
Excessive sebum production (seborrhea)

Acne is still a very underserved market with treatment options that are only marginally effective. Only one product, oral Accutane® (isotretinoin) that reduces sebum production has been highly effective, but at the expense of a black box warning with significant side effects including teratogenicity that require extensive patient monitoring. Accutane® is indicated only for acne which is severe and recalcitrant to other treatment.

Topical therapy is often preferred over oral therapy because of the reduced risk for adverse systemic effects. The most common topical drugs for acne can be divided into the following categories:
Retinoids (i.e., tazarotene, tretinoin, adapalene)
Antibiotics (i.e., clindamycin)
Benzoyl peroxide (BPO)
Others (i.e., dapsone, azelaic acid)

While many topical therapies are available, none of them address all four factors and most specialize in a few of these factors. Currently, no topical therapies in the market address excessive sebum production. Sebum is produced by the sebaceous gland, which is an appendage of the hair follicle, so it makes sense to target the sebaceous gland for more effective therapy. Since *P. acnes* depends on sebum to live, reduction of sebum is also thought to indirectly reduce *P. acnes*.

Topical retinoids primarily act by normalizing infundibular hyperkeratinization and reducing inflammation, hence topical retinoids remain a mainstay for treatment of mild-to-moderate acne. The current topical retinoid formulations do not inhibit sebum production and their use is often limited by local tolerability (i.e., skin irritation).

There is a need in the art, therefore, for topical compositions capable of reducing sebum production and treating the conditions associated with it.

SUMMARY OF THE INVENTION

The present invention provides topical dermal compositions including microsphere encapsulated isotretinoin. Pharmaceutically acceptable salts, esters, or amides of isotretinoin are also contemplated for use in the practice of the invention. The compositions of the invention are useful for treating a variety of conditions associated with excess sebum production, such as, for example, acne.

By employing the compositions and methods of the invention, isotretinoin can be delivered deep into the hair follicle where it will be converted to the active tretinoin to reach the sebaceous gland. Since isotretinoin itself has much lower activity on the retinoid receptor (RAR), the compositions of the invention provide reduced side effects on the surface of the skin in comparison to other retinoids currently used for topical treatment of acne.

In one embodiment of the invention, there are provided topical dermal compositions including a plurality of particles, wherein the particles include
a) a biodegradable polymer, and
b) isotretinoin, or a pharmaceutically acceptable salt, ester, or amide thereof;
wherein the particles have an average diameter between about 0.1 µm and about 10 µm.

In another embodiment of the invention, there are provided methods for treating a condition associated with excess sebum production. Such methods can be performed, for example, by topically applying to the skin of a patient in need thereof a composition of the invention.

DETAILED DESCRIPTION OF THE INVENTION

Figure 1:
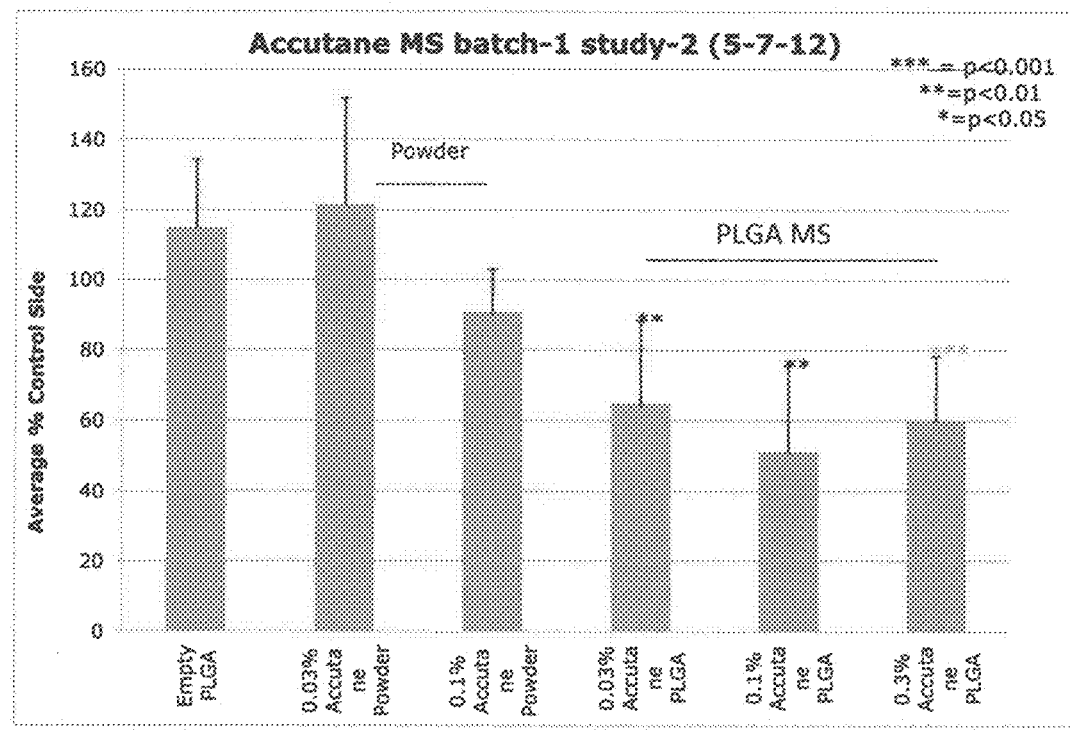
FIGS. 1 and 2 set forth data which demonstrates that PLGA polymer encapsulated Accutane substantially reduced sebaceous gland in the hamster flank organ model when compared to Accutane drug powder (MS=microsphere).

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

The invention provides topical dermal compositions including a plurality of particles,
 wherein the particles include
  a) a biodegradable polymer, and
  b) isotretinoin, or a pharmaceutically acceptable salt, ester, or amide thereof;
 wherein the particles have an average diameter between about 0.1 μm and about 10 μm.

In some embodiments, the particles have an average diameter no greater than about 5 μm. In some embodiments, the particles have an average diameter no greater than about 4 μm. In some embodiments, the particles have an average diameter no greater than about 1 μm.

Biodegradable polymers contemplated for use in the practice of the invention include, but are not limited to, poly hydroxyaliphatic carboxylic acids, polyesters, polysaccharides, and combinations thereof. In some embodiments, the biodegradable polymer is poly(lactic-co-glycolic acid) (PLGA).

The term "ester" refers to any compound falling within the definition of that term as classically used in organic chemistry. It includes organic and inorganic esters.

Unless stated otherwise in this application, esters are derived from the saturated aliphatic alcohols or acids of ten or fewer carbon atoms or the cyclic or saturated aliphatic cyclic alcohols and acids of 5 to 10 carbon atoms. Examples include aliphatic esters derived from lower alkyl acids and alcohols, and phenyl or lower alkyl phenyl esters.

The term "amide" has the meaning classically accorded that term in organic chemistry. In this instance it includes the unsubstituted amides and all aliphatic and aromatic mono- and di-substituted amides. Examples include the mono- and di-substituted amides derived from the saturated aliphatic radicals of ten or fewer carbon atoms or the cyclic or saturated aliphatic-cyclic radicals of 5 to 10 carbon atoms. In one embodiment, the amides are derived from substituted and unsubstituted lower alkyl amines. In another embodiment, the amides are mono- and disubstituted amides derived from the substituted and unsubstituted phenyl or lower alkylphenyl amines. One may also use unsubstituted amides.

"Acetals" and "ketals" include the radicals of the formula-CK where K is $(-OR)_2$. Here, R is lower alkyl. Also, K may be $-OR_7O-$ where $R_7$ is lower alkyl of 2-5 carbon atoms, straight chain or branched.

Pharmaceutically acceptable salts of isotretinoin are also contemplated for use in the practice of the invention. A pharmaceutically acceptable salt is any salt which retains the activity of the parent compound and does not impart any deleterious or untoward effect on the subject to which it is administered and in the context in which it is administered.

Pharmaceutically acceptable acid addition salts of isotretinoin are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The particles included in the compositions of the invention have an average diameter no less than about 0.1 μm and no greater than about 10 μm In one embodiment, the particle is shaped like a sphere. The inventors refer to such particles as "microspheres," even though they may have an average diameter in the nanometer range (that is, about 100 nm to about 999 nm). The microspheres of the invention have a maximum average diameter of about 10 μm.

As used here, the term "about," when used in connection with a value, means that the value may not differ by more than 5%. Hence, "about 10 μm" includes all values within the range of 9.5 μm to 10.5 μm.

In one embodiment, the microspheres of the invention have a maximum average diameter of about 10 μm. In another embodiment, the microspheres of the invention have a maximum average diameter of about 9 μm. In another embodiment, the microspheres of the invention have a maximum average diameter of about 8 μm. In another embodiment, the microspheres of the invention have a maximum average diameter of about 7 μm. In another embodiment, the microspheres of the invention have a maximum average diameter of about 6 μm. In another embodiment, the microspheres of the invention have a maximum average diameter of about 5 μm. In another embodiment, the microspheres of the invention have a maximum average diameter of about 4 μm. In another embodiment, the microspheres of the invention have a maximum average diameter of about 3 μm. In another embodiment, the microspheres of the invention have a maximum average diameter of about 2 μm. In another embodiment, the microspheres of the invention have a maximum average diameter of about 1 μm.

In another embodiment, the microspheres of the invention have a maximum average diameter less than about 1 µm. In another embodiment, the microspheres of the invention have a maximum average diameter of about 0.9 µm. In another embodiment, the microspheres of the invention have a maximum average diameter of about 0.8 µm. In another embodiment, the microspheres of the invention have a maximum average diameter of about 0.7 µm. In another embodiment, the microspheres of the invention have a maximum average diameter of about 0.6 µm. In another embodiment, the microspheres of the invention have a maximum average diameter of about 0.5 µm. In another embodiment, the microspheres of the invention have a maximum average diameter of about 0.4 µm. In another embodiment, the microspheres of the invention have a maximum average diameter of about 0.3 µm. In another embodiment, the microspheres of the invention have a maximum average diameter of about 0.2 µm. In another embodiment, the microspheres of the invention have a maximum average diameter of about 0.1 µm.

In one embodiment, the particle is shaped like a cylindrical rod. The inventors refer to such particles as "microcylinders," even though they may have an average diameter in the nanometer range (that is, about 100 nm to about 999 nm). The microcylinders of the invention have a maximum average diameter and maximum average length such that no one such dimension is greater than about 10 µm. In other embodiments, the particles of the invention are of different geometry, such as fibers or circular discs; any geometry falls within the scope of the invention, as long as the average of any single dimension of the particle exceeds about 10 µm.

In one embodiment, the microcylinders of the invention have a maximum average diameter of about 10 µm. In another embodiment, the microcylinders of the invention have a maximum average diameter of about 9 µm. In another embodiment, the microcylinders of the invention have a maximum average diameter of about 8 µm. In another embodiment, the microcylinders of the invention have a maximum average diameter of about 7 µm. In another embodiment, the microcylinders of the invention have a maximum average diameter of about 6 µm. In another embodiment, the microcylinders of the invention have a maximum average diameter of about 5 µm. In another embodiment, the microcylinders of the invention have a maximum average diameter of about 4 µm. In another embodiment, the microcylinders of the invention have a maximum average diameter of about 3 µm. In another embodiment, the microcylinders of the invention have a maximum average diameter of about 2 µm. In another embodiment, the microcylinders of the invention have a maximum average diameter of about 1 µm.

In another embodiment, the microcylinders of the invention have a maximum average diameter less than about 1 µm. In another embodiment, the microcylinders of the invention have a maximum average diameter of about 0.9 µm. In another embodiment, the microcylinders of the invention have a maximum average diameter of about 0.8 µm. In another embodiment, the microcylinders of the invention have a maximum average diameter of about 0.7 µm. In another embodiment, the microcylinders of the invention have a maximum average diameter of about 0.6 µm. In another embodiment, the microcylinders of the invention have a maximum average diameter of about 0.5 µm. In another embodiment, the microcylinders of the invention have a maximum average diameter of about 0.4 µm. In another embodiment, the microcylinders of the invention have a maximum average diameter of about 0.3 µm. In another embodiment, the microcylinders of the invention have a maximum average diameter of about 0.2 µm. In another embodiment, the microcylinders of the invention have a maximum average diameter of about 0.1 µm.

In one embodiment, the microcylinders have a maximum average length of about 10 µm, about 9 µm, about 8 µm, about 7 µm, about 6 µm, about 5 µm, about 4 µm, about 3 µm, about 2 µm, about 1 µm, about 0.9 µm, about 0.8 µm, about 0.7 µm, about 0.6 µm, about 0.5 µm, about 0.4 µm, about 0.3 µm, or about 0.2 µm.

The size and geometry of the particle can also be used to control the rate of release, period of treatment, and drug concentration. Larger particles will deliver a proportionately larger dose, but, depending on the surface to mass ratio, may have a slower release rate.

The retinoid of the invention may be in a particulate or powder form. In one embodiment, the retinoid itself consists of particles having the dimensions described above.

In another embodiment, isotretinoin is combined with a biodegradable polymer. In one embodiment, isotretinoin is from about 10% to about 90% by weight of the composition. In another embodiment, isotretinoin is from about 20% to about 80% by weight of the composition. In another embodiment, isotretinoin is from about 30% to about 70% by weight of the composition. In another embodiment, isotretinoin is from about 40% to about 60% by weight of the composition. In one embodiment, isotretinoin comprises about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the composition.

Suitable polymeric materials for use in the compositions of the invention include those materials which are biocompatible with the skin so as to cause no substantial irritation or other side effects. In one embodiment, such materials are at least partially biodegradable. In another embodiment, such materials are completely biodegradable.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, CRC Critical Reviews in Therapeutic Drug Carrier Systems, Vol. 1, CRC Press, Boca Raton, Fla. 1987, pp 39-90 (*Biodegradable Polymers in Controlled Drug Delivery*), the contents of which are incorporated herein by reference, which describes encapsulation for controlled drug delivery, may find use in the present compositions.

Of additional interest are polymers of hydroxyaliphatic carboxylic acids, either homopolymers or copolymers, and polysaccharides, lipid nanoparticle, and mesoporous silica nanoparticle. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Lipid nanoparticles contemplated for use in the practice of the invention include, but are not limited to, Crodamol MM, Crodamol SS, myristyl myristate and myristyl laurate (Ceraphyl 424), triglycerides of $C_{10}$-$C_{18}$ fatty acids (Gelucire 43/01), and propylene glycol monopalmitostearate (Monosteol).

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic compound, ease of use of the polymer in making the compositions of the present invention, a half-life in the physiological environment of at least about 6 hours, preferably greater than about one day, and water insolubility.

The biodegradable polymeric materials which are included to form the particles are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the system is the relative average molecular weight of the polymeric composition employed in the system. Different molecular weights of the same or different polymeric compositions may be included in the system to modulate the release profile. In certain systems, the relative average molecular weight of the polymer will range from about 9 to about 64 kD, from about 10 to about 54 kD, or from about 12 to about 45 kD.

In some compositions, copolymers of glycolic acid and lactic acid (poly(lactic-co-glycolic acid)) are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the drug delivery system, where a more flexible system is desirable for larger geometries. The proportion of polylactic acid in the polylactic acid polyglycolic acid (PLGA) copolymer can be 0-100%; in other embodiments, the proportion of polylactic acid can be from about 10% to about 90%, from about 20% to about 80%, from about 30% to about 70%, or from about 40% to about 60%. In one embodiment, the proportion of polylactic acid may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the composition.

The biodegradable polymer of the composition of the invention may comprise a mixture of two or more biodegradable polymers. For example, the composition may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the systems surface, dissolution, diffusion through porous channels of the hydrated polymer and erosion. Erosion can be bulk or surface or a combination of both.

One example of a composition of the invention includes isotretinoin with a biodegradable polymer matrix that comprises a (lactide-co-glycolide) or a poly(D,L-lactide-co-glycolide). The composition system may have an amount of isotretinoin from about 40% to about 70% by weight of the system.

The release of isotretinoin from the composition may include an initial burst of release followed by a gradual increase in the amount of isotretinoin released, or the release may include an initial delay in release of isotretinoin followed by an increase in release. When the biodegradable polymer is substantially completely degraded, the percent of isotretinoin that has been released is about one hundred percent.

It may be desirable to provide a relatively constant rate of release of isotretinoin from the particles. However, the release rate may change to either increase or decrease depending on the formulation of the particle. In addition, the release profile of isotretinoin may include one or more linear portions and/or one or more non-linear portions. In one embodiment, the release rate is greater than zero once the system has begun to degrade or erode.

The particles of the invention may be monolithic, that is, having the active agent or agents homogenously distributed through the polymer, or encapsulated, where a reservoir of active agent is encapsulated by the polymer. Due to ease of manufacture, monolithic systems are usually preferred over encapsulated forms. However, the greater control afforded by the encapsulated, reservoir-type implants may be of benefit in some circumstances, where the therapeutic level of the drug falls within a narrow window. In addition, isotretinoin, may be distributed in a non-homogenous pattern in the polymer. For example, a particle may include a portion that has a greater concentration of the isotretinoin relative to a second portion of the implant.

Thus, particles can be prepared where the center may be of one material and the surface may have one or more layers of the same or a different material, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve.

The proportions of isotretinoin, polymer, and any other modifiers may be empirically determined by formulating several drug delivery systems with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to isotretinoin and polymer, the particles disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total drug delivery system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from about 0.001% to about 5% by weight; in another embodiment, they may be present in amounts from about 0.01% to about 2% by weight.

In addition, the particles may include a solubility enhancing compound provided in an amount effective to enhance the solubility of isotretinoin relative to substantially identical systems without the solubility enhancing compound. For example, an implant may include a β-cyclodextrin, which is effective in enhancing the solubility of isotretinoin. The β-cyclodextrin may be provided in an amount from about 0.5% (w/w) to about 25% (w/w) of the particle. In other embodiments, the β-cyclodextrin is provided in an amount from about 5% (w/w) to about 15% (w/w) of the particle.

Additionally, release modulators such as those described in U.S. Pat. No. 5,869,079, the contents of which are incorporated herein by reference, may be included in the particles. The amount of release modulator employed will be dependent on the desired release profile, the activity of the modulator, and on the release profile of isotretinoin in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce the particles described herein. In one embodiment, particles are produced using a solvent evaporation process. Such a process may include steps of liquid sieving, freeze drying, and sterilizing the various composition compounds. In one embodiment, isotretinoin and a polymer are combined with methylene chloride to form a first composition, and water and polyvinyl alcohol are combined to form a second composition. The first and second compositions are combined to form an emulsion. The emulsion is rinsed and/or centrifuged, and the resulting product dried. In a further embodiment, the emulsion undergoes an evaporation process to remove methylene chloride from the emulsion. For example, the emulsion can be evaporated for about 2 days or more. In this embodiment, the method includes sieving isotretinoin-containing microspheres in a liquid phase, as compared to a method which includes sieving isotretinoin-containing microparticles in a dry phase. This method can also comprise a step of freeze drying the sieved microparticles, and a step of packaging the freeze dried microparticles.

In another embodiment, a method of producing isotretinoin-containing microspheres includes one or more of the following steps. In certain embodiments, the method includes each of the following steps. A polymeric material, such as PLGA, is dissolved in a solvent, such as methylene chloride. The dissolving of the PLGA can occur with stirring the mixture until the PLGA is completely dissolved. A predetermined amount of isotretinoin is added to the dissolved PLGA composition. The resulting composition can be understood to be a first composition in reference to this method. A second different composition is produced by combining heated water, for example water having a temperature of about 80° C., with polyvinylic alcohol (PVA). The PVA can be combined with the heated water by stirring the water at a rate effective in maintaining PVA in suspension without substantial bubble formation. The second composition may then be cooled to a desired temperature, such as room temperature.

An emulsion can be produced by combining the first composition and the second composition described in the preceding paragraph. For example, the second composition (i.e., the PVA solution) can be vigorously stirred while avoiding bubble formation. While stirring the second composition, the first composition is added to form an emulsion. As the mixture emulsifies, the stirring speed may be increased to keep the surface of the emulsion moving. Foam or bubble formation is minimized during these steps. In this method, the emulsion is stirred for at least two days (e.g., for about 48 hours or more). As the emulsion is stirred for about 24 hours, the emulsion begins to liquefy. To reduce the possibility of foaming, the stirring speed can be decreased as the emulsion liquefies. After about 48 hours, methylene chloride is substantially or completely evaporated. The method can include a step of determining the amount of methylene chloride in the evaporated material.

After the evaporation of the methylene chloride, the microparticle-containing composition is rinsed and sieved. For example, the microparticle-containing composition is combined with a liquid and centrifuged. The supernatant is removed and the pellet can be resuspended by sonication or other suitable method for additional centrifugation steps. After the microsphere suspension has been centrifuged, water can be added to rinse the microspheres, and the resulting supernatant can be removed by vacuum extraction. In some methods, at least three water rinsing steps are desirable. The rinsed pellets are then sieved through a plurality of filters. For example, the pellets can be passed through two superimposed filters having a pore size of about 125 μm and about 45 μm, respectively. The filters can be rinsed with water and the solution can be retrieved in the filter bottom.

The retrieved solution can then be combined with an additional amount of water and rinsed two or more times using a centrifuge. The rinsed pellet can then be placed in the filter bottom and covered with a filter to reduce loss of the microsphere material during a lyophilization process. The material is then frozen. For example, the material is frozen at −50° C. and freeze dried for at least twelve hours. After freeze drying, the microspheres can be stored in a package, and/or may be sterilized by a sterilization device, such as a source of gamma radiation.

Additional examples of methods for producing isotretinoin-containing particles are described in U.S. Patent Application Publication No. 2011/0076318. Additional examples of producing particles of biodegradable polymer may be found in U.S. Patent Application Publication No. 2005/0003007 and No. 2008/0182909, the contents of both of which are incorporated herein by reference.

In one embodiment, the compositions of the invention may be used to treat conditions associated with excess sebum production. Such conditions include, for example, acne vulgaris, seborrhoeic dermatitis, keratosis pilaris.

In another embodiment, the compositions of the invention may be used to treat those conditions in which it would be beneficial to suppress the function of the sebaceous gland. Such conditions include, for example, sebaceous cyst, sebaceous hyperplasia, sebaceous adenoma, and sebaceous gland carcinoma.

The following examples are intended only to illustrate the invention and should in no way be construed as limiting the invention.

EXAMPLES

Figure 2:
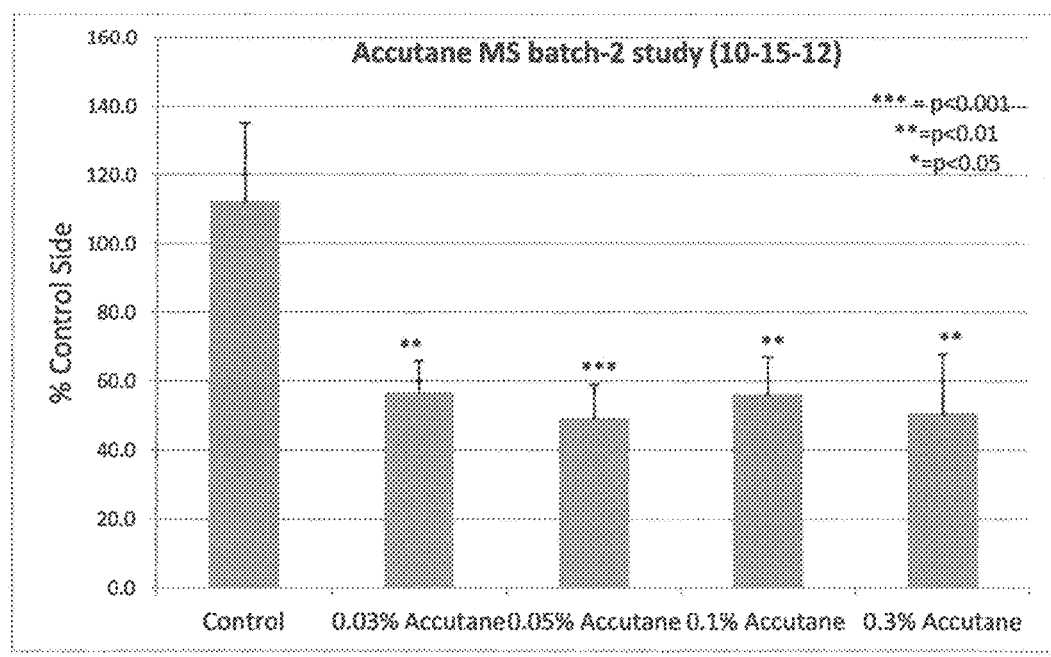
Figure 3:
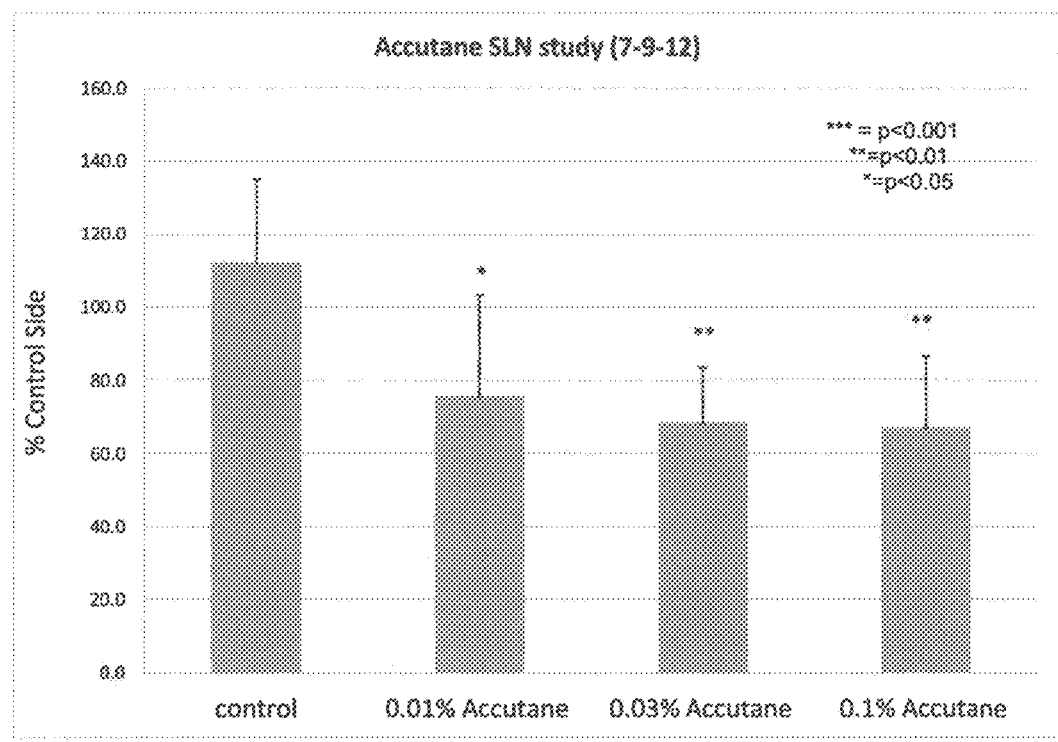
FIG. 3 sets forth data which demonstrates that solid lipid nanoparticle (SLN) encapsulated Accutane reduced sebaceous gland significantly in the hamster model when compared to the drug powder.

The data presented in FIGS. 1-3 was generated using the following invention microsphere encapsulated Accutane batches:
Accutane MS
  Batch-1: 1.7 μm, 8% drug load
  Batch-2: 0.9 μm, 25% drug load
Accutane solid lipid nanoparticle (SLN)
  Batch-1: 2.1 μm, 10% drug load.
Animals and Treatment Procedure Male hamsters weighing about 110-120 g were used. The animals arrived at least 7 days before the study and were single-housed. Animals were randomized by weight. The right side flank was shaved to expose the flank organ, removing as much hair as possible, and the animals were wiped clean with a cotton swab soaked with 70% ethanol.

Drug formulations were carefully spread over the flank organ with a pipette. Before applying the drug each time, the flank organ area was wiped clean with a cotton swab soaked with 70% ethanol. The animals were treated in this manner 5 days/week for 26 days. If hair grew back on the flank organ, the hair was shaved.
Tissue Processing and Analysis The animals were sacrificed with $CO_2$. The flank organ was shaved, cleaned, and excised. The flank organ was attached to a paper card, put it into a thick cassette, overlayed with a piece of sponge, and closed. The cassette was air dried for a few minutes before being placed into 10% formalin (buffered) for fixation.

The organ was cut at the middle to make 15-20 μm slices, the slices were placed onto glass slides, and then stained with hematoxylin and eosin. The slides were scanned with NanoZoomer® to obtain clear pictures and the sebaceous gland areas were measured with the software accompanying the NanoZoomer®.

A pair wise t-TEST was used to compare treated sides against untreated control sides.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topical dermal composition comprising a plurality of particles, wherein the particles comprise
   a) a biodegradable polymer, and
   b) isotretinoin, or a pharmaceutically acceptable salt, ester, or amide thereof;
      wherein the particles have a maximum average diameter of about 1 μm;
      wherein the biodegradable polymer comprises lipid nanoparticles, and
      wherein the lipid nanoparticles comprise myristyl myristate, myristyl laurate, triglycerides of $C_{10}$-$C_{18}$ fatty acids, and propylene glycol monopalmitostearate.

2. The composition of claim 1, wherein the particles are spheres.

3. The composition of claim 1, wherein the particles are cylinders.

4. A method for treating a condition associated with excess sebum production,
   the method comprising topically applying to the skin of a patient in need of such treatment the composition of claim 1.

5. The method of claim 4, wherein the condition is selected from the group consisting of: acne vulgaris, seborrhoeic dermatitis, and keratosis pilaris.

6. The method of claim 4, wherein the composition provides for an extended release of the compound.

* * * * *